United States Patent [19]

Kaufman et al.

[11] Patent Number: 4,762,571
[45] Date of Patent: Aug. 9, 1988

[54] EXPENDABLE IMMERSION DEVICE FOR COMBINING AN EXPENDABLE IMMERSION SENSOR AND MOLTEN METAL SAMPLER

[75] Inventors: Edwin E. Kaufman, Ambler; William E. Shuttleworth, Ellwood; John R. Wiese, Pittsburgh, all of Pa.

[73] Assignee: General Signal Corporation, Stamford, Conn.

[21] Appl. No.: 839,852

[22] Filed: Mar. 14, 1986

[51] Int. Cl.[4] .......................................... H01L 35/02
[52] U.S. Cl. ................................. 136/234; 136/235
[58] Field of Search .......................... 136/231–234, 136/218–222

[56] References Cited

U.S. PATENT DOCUMENTS

| | | | |
|---|---|---|---|
| 3,024,295 | 3/1962 | Moore | 136/234 |
| 3,455,164 | 7/1969 | Boyle | 136/234 |
| 3,463,005 | 8/1969 | Hance | 136/234 |
| 3,685,359 | 8/1972 | Boron et al. | 136/234 |
| 3,756,082 | 9/1973 | Bardenheuer et al. | 136/234 |
| 3,915,002 | 10/1975 | Hance | 73/354 |
| 3,950,992 | 4/1976 | Hance | 73/354 |
| 3,992,916 | 12/1975 | Wickert | 73/354 |
| 4,229,230 | 10/1980 | Hance | 136/234 |

FOREIGN PATENT DOCUMENTS 53-56326 7/1978 Japan .

Primary Examiner—Deborah L. Kyle
Assistant Examiner—T. J. Wallen
Attorney, Agent, or Firm—Robert R. Hubbard; Joseph P. Abate; William G. Miller, Jr.

[57] ABSTRACT

There is provided an expendable device for use with a standard immersion sensor for a molten metal bath to simultaneously hold a standard immersion sampler in juxtaposition to the sensor when the sensor is in its protective sleeve at the end of a lance ready for immersion into the bath. This device provides another expendable heat insulating protective sleeve for accepting in its end the sampler with means being provided for maintaining a side by side relationship between the sampler sleeve and the sensor sleeve during immersion. This combination may advantageously have a vent pipe extending between the sleeves to allow air displaced from the sampler by influx of the sample to vent to a region above the molten metal bath by way of a passage in the sensor sleeve.

4 Claims, 2 Drawing Sheets

EXPENDABLE IMMERSION DEVICE FOR COMBINING AN EXPENDABLE IMMERSION SENSOR AND MOLTEN METAL SAMPLER

BACKGROUND OF THE INVENTION

This invention relates to expendable immersion devices of the type which are inserted into a bath of molten metal and used to measure a characteristic of the bath, as with a temperature sensor and to obtain simultaneously a sample of the bath for subsequent analysis. It is routine in the practice of making and refining molten metals and alloys to measure specific characteristics of the molten metal, such as temperature, dissolved oxygen content, carbon content, etc. with separate measuring elements individually immersed into the molten metal bath during the melting period. It is also routine practice to obtain a sample of the molten metal during the melting period for chemical analysis at a later time. Such a sample is normally taken by either pouring a sample of the molten metal into an appropriate mold or by immersing an expendable immersion sampler into the molten metal bath. These immersion samplers are usually vented cavities which freeze a sample of the molten metal which flows in after a fusible cap covering the cavity has melted.

Immersion assemblies for molten metal have been constructed to utilize expendable immersion pyrometer elements for measuring and to also include a cavity for freezing a sample of the molten metal. The sample cavity in these prior art devices is constructed as part of the pyrometer element and is arranged to be insertable into a protective sleeve which normally protects the end of the lance used for manipulating the device into the molten metal bath. The sample cavity is oriented in line with the temperature measuring element. Access to the cavity is sometimes provided on the side of the sleeve and sometimes through the end of the sleeve through the same opening as that used by the temperature measuring element. In all of these prior art structures, the combination units are more complex than the standard sensors or samplers and therefore are expensive elements. Such special elements have a limited use in that their expense dictates that they not be used unless simultaneous measurement and sampling are needed. Thus, it is necessary to have available the standard expendable immersion pyrometer elements and standard sampling elements as well as the special dual purpose elements for economical operation during those times when a sample is not needed simultaneously with a measurement.

It is an object of this invention to provide a device for simultaneously making a measurement of a characteristic of a molten metal sample as well as for taking a sample of the bath.

It is also an object of this invention to provide a device for simultaneously measuring a characteristic of a molten metal bath and taking a sample of that bath using standard elements so that the expense of maintaining an inventory of special elements is minimized while providing the flexibility of separately making a measurement or taking a sample, or doing both simultaneously.

SUMMARY OF THE INVENTION

The present invention provides an expendable device for simultaneously holding a standard immersion sampler in juxtaposition to a standard immersion sensor when the sensor is inserted in its protective sleeve at the end of a lance for immersion into a molten metal bath. This device provides another expendable heat insulating protective sleeve for accepting in its end an immersion sampler with means being provided for maintaining a side by side relationship between the sampler sleeve and the sensor sleeve during immersion. This combination may advantageously have a vent pipe extending between the sleeves to allow air displaced from the sampler by influx of the sample to vent to a region above the molten metal bath through the sensor sleeve.

DESCRIPTION OF THE PREFERRED EMBODIMENTS

Expendable immersion assemblies for measuring a characteristic of a molten metal bath are usually constructed in a manner similar to the structure shown in U.S. Pat. No. 3,024,295 issued to Philemon J. Moore on Mar. 6, 1962, on an immersion pyrometer. These assemblies include a lance with a manipulator section usually including of a long piece of iron pipe, which carries the leadwire necessary to connect the measuring element to a measuring instrument. The manipulator section has its immersion end protected by a heat insulating tube or sleeve, usually cardboard, which slides over the end of the manipulator section so that it will not be damaged during immersion of the measuring element in the molten metal bath. The open end of the cardboard tube which extends beyond the end of the manipulator section forms the recepticle for receiving an insertable primary element such as an expendable thermocouple, in such a way that it connects to the leadwire while preventing the flow of molten metal into the sleeve. The primary element may be held in the tube with a cement, if necessary.

Figure 1:
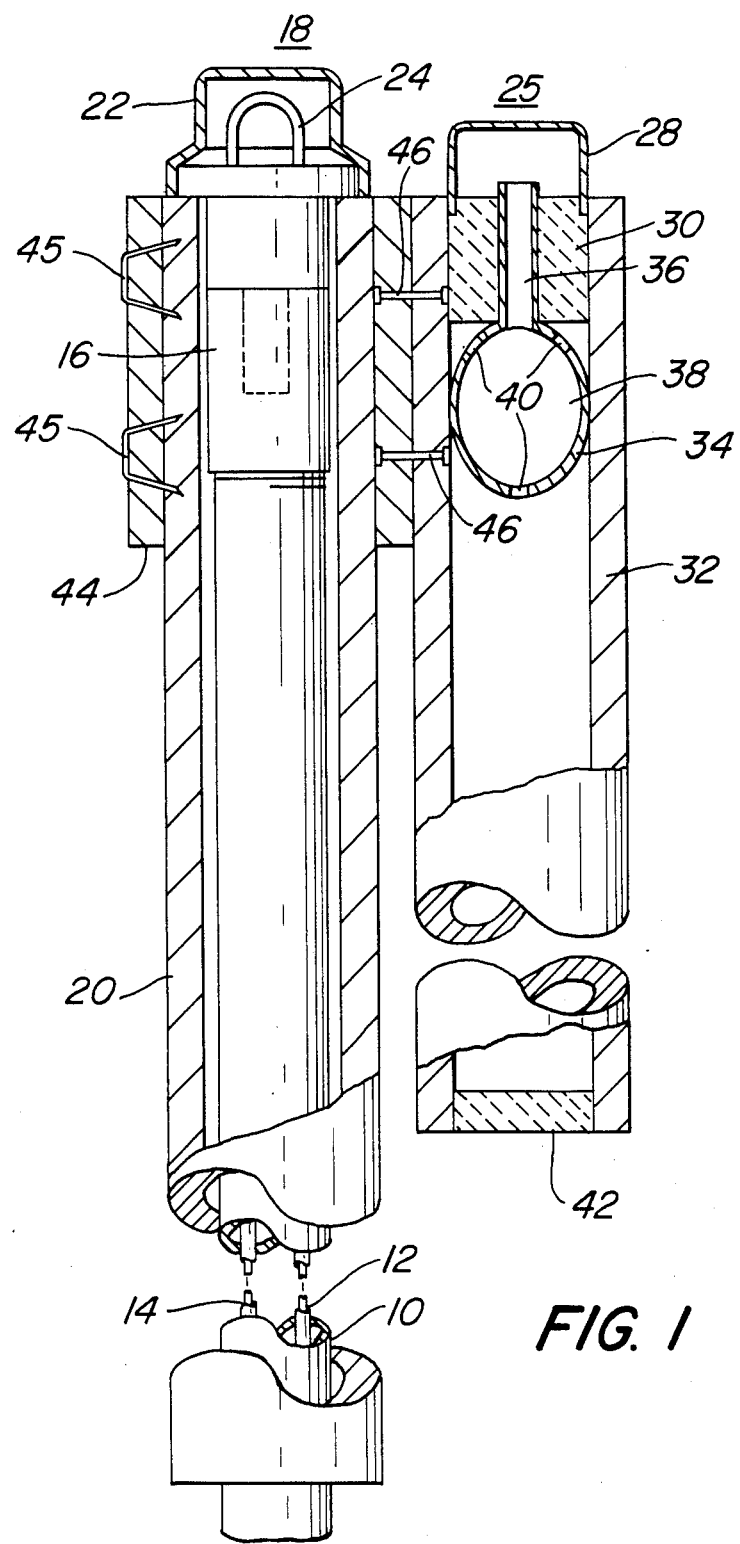
FIG. 1 is an elevation of one variation on the novel structure in which the sleeve holding the sampler is adapted to be a sliding fit over a standard sleeve of an expendable immersion sensor.

In FIG. 1 a typical immersion pyrometer is shown as including a length of iron pipe 10, which is the immersion end of the manipulator section of a immersion lance which will normally have at its other end a handlearrangement (not shown). This length of pipe carries the leadwires 12 and 14 which connect between an associated measuring instrument, not shown, and an insulator 16 fixed on the threaded end of pipe 10 of receiving the ends of the leadwire in a manner such that they may make contact with an insertable element such as the expendable pyrometer 18, shown inserted into the end of the cardboard protecting tube 20 One form which the expendable pyrometer 18 can take it that shown in U.S. Pat. No. 4,229,230 issued to Richard J. Hance on Oct. 21, 1980. The end of the element 18 has a fusible cover 22 which melts after immersion into the molten metal bath below any slag layer to expose the thermocouple protection tube 24 and hence the thermocouple it protects to the heat of the molten metal.

In order to obtain a sample of the molten metal at the same time that the temperature of the bath is being measured, it is convenient to add a standard immersion sampler such as the end filling sampler 25 which includes a fusible cover 28 imbedded in a ceramic plug 30 in the end of a heat insulating protective sleeve 32. The cover prevents the slag of a molten steel bath from entering the sampler as the lance is inserted into the bath. The ceramic plug 30 carries a vented metal sample enclosure 34. The enclosure 34 has an elongated, tube like, end 36 which is held by the plug 30. This end extends from the main part of the enclosure, namely the spherical metal cavity 38 and receives the molten metal when the fusible cover 28 has melted, thus filling the spherical cavity 38. As has been noted, the cavity 38 has vent holes, such as 40, which allow air in the cavity to exit into the interior of the sleeve 32 and become compressed behind the cavity as the sample flows into the cavity. As is shown, the other end of the sleeve 32 is plugged by a ceramic plug 42. The sleeve 32 must, of course, be long enough to allow an adequate sample to be collected without being hindered by the compression of the air.

The sampler unit 25 is held in a side by side relationship with the immersion pyrometer 18 by means of the mounting sleeve 44, normally of cardboard, which is held to the sleeve 32 by rivets 46. The sleeve 44 is a slip fit over the sleeve 20 so that when it is determined that a sample is necessary as well as a temperature measurement, the operator who is making the immersion of the lance may merely slide a sampler unit 25 with its additional mounting tube 44 onto a standard immersion pyrometer assembly to make the measurement and obtain the sample simultaneously.

Figure 3:
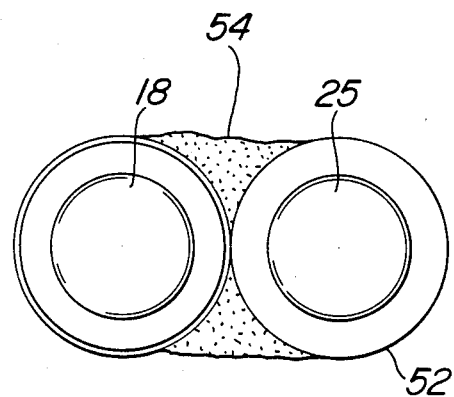
FIG. 3 is an end view of the device of FIG. 2 showing the cement which can be used to assist in maintaining the sleeves in a side by side relationship.

The sleeve 44 can be held fast to the sleeve 20, after it has been slipped over sleeve 20, by means of staples 45, as shown, or by other fastening devices, and may be supplemented by a coating of refractory cement on the exterior, much as is shown in FIG. 3, to be described.

Figure 2:
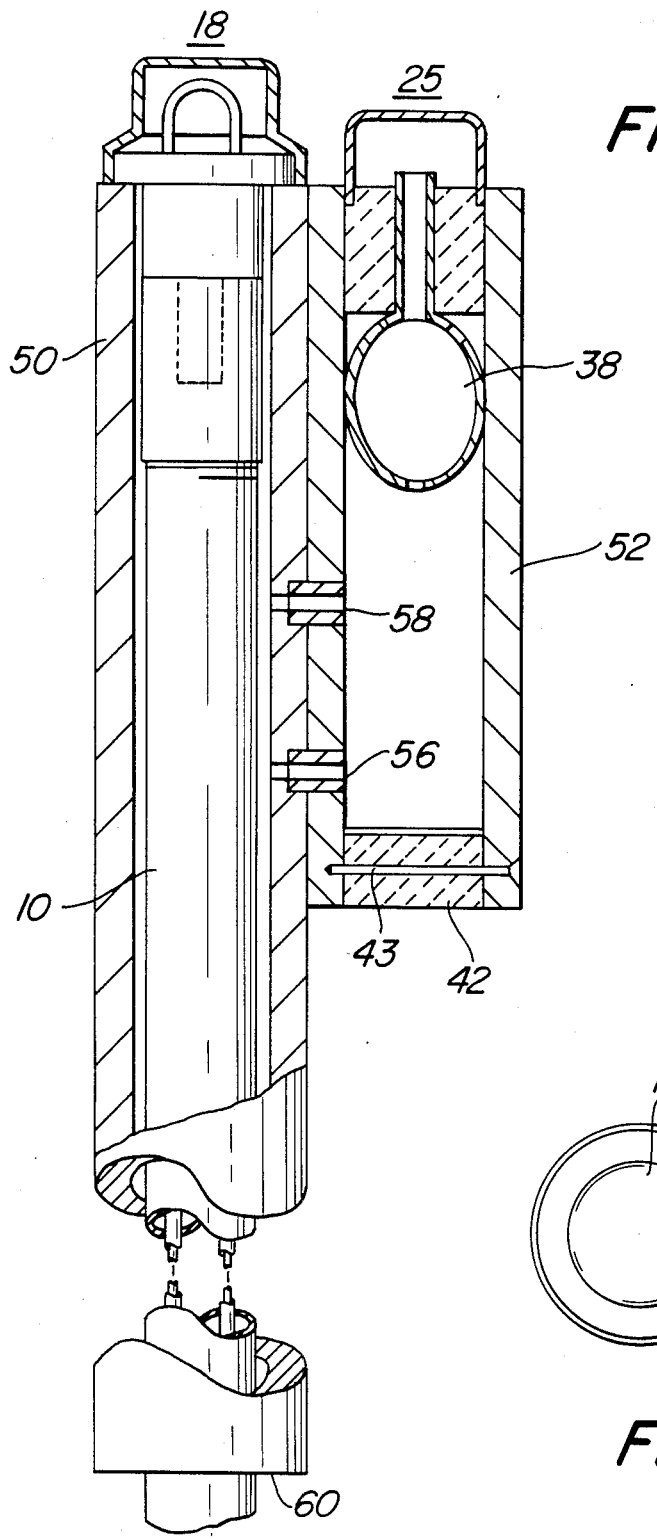
FIG. 2 is an elevation of another variation of the novel device showing side by side sleeves with an inserted temperature measuring element and an inserted sampling element as they would appear when assembled to a lance for immersion.

It may be advantageous to provide a means for venting the air displaced from the sample enclosure to a region above the bath instead of allowing it to compress. In that case it is desirable to utilize the arrangement shown in FIG. 2. In such an arrangement the cardboard sleeve 50 protecting the manipulator section of the lance is made a part of an expendable device which will hold both the sensor and the sampler of the assembly. Thus, the cardboard sleeve 50 is placed in side by side relationship to the sleeve 52, which receives in its one end the sampler unit 25, and which has its other end plugged by a ceramic plug 42, shown as being held by a nail 43.

The side by side relationship of the sleeves 50 and 52 is maintained by the use of a refractory cement 54 (FIG. 3) which surrounds the juncture between the two sleeves. In addition the sleeves 50 and 52 are held together by the metal vent tubes 56 and 58 which connect the interior of the sleeve 52 to the interior of the sleeve 50 so that air displaced from the sample cavity 38 will flow into the interior of sleeve 50 and thence to the end of that sleeve 60 which is above the molten metal bath. This flow is, of course, possible because of the passage provided by the space between the exterior of the pipe 10 and the interior of the sleeve 50.

What is claimed is:

1. An expendable device for holding an insertable immersion sensor and an insertable immersion sampler to a lance having a manipulator section carrying electrical leads which must be connected to said sensor when said sensor and sampler are immersed into a bath of molten metal, comprising:

an immersion sensor for measuring a characteristic of said bath;

an end filling immersion sampler for gathering a sample of the molten metal of said bath while said device is immersed therein;

a first expendable heat insulating protective sleeve adapted to fit over said manipulator section for protecting said manipulator during immersion, providing a passage for gases from the interior of said first sleeve to a region above the bath, and holding at one end thereof said insertable immersion sensor so that said sensor seals the interior of said sleeve from said molten metal and maintains electrical contact between said sensor and said connecting leads;

a second expendable heat insulating protective sleeve adapted to hold said insertable sampler in one end thereof and having its other end plugged;

means for attaching said second sleeve in a side by side relationship to said first sleeve; and venting means providing a connecting passage between the interiors of said first and second sleeves so that air from said sampler is vented from said second sleeve for passage through said first sleeve to a region above said bath as said molten metal enters the sampler.

2. An expendable device as set forth in claim 1 in which said immersion sensor is an immersion thermocouple for measuring the temperature of said bath.

3. An expendable device as set forth in claim 2 in which said venting means has at least one tube extending between said sleeves and fixedly mounted in the walls of said sleeves, and the means for supporting said second sleeve in side by side relationship with said first sleeve is said venting means and refractory cement along the exterior of the junction between said first and second sleeves.

4. An expendable device for holding an immersion sensor and an immersion sampler to a manipulator section of a lance for immersing said sensor and sampler into a molten metal bath, comprising:

a first expendable heat insulating protective sleeve adapted to fit over said manipulator section for protecting said manipulator during immersion, and holding at one end thereof said immersion sensor so that said sensor seals the interior of said sleeve from said molten metal and maintains electrical contact between said sensor and said connecting leads;

a passage in said first sleeve providing for the passage of gases from the interior of said first sleeve to a region above the bath;

a second expendable heat insulating protective sleeve having one end closed and the other end adapted to hold said sampler;

means for supporting said second sleeve in a side by side relationship with said first sleeve; and venting means providing a connecting passage between the interiors of said first and second sleeves so that air displaced from said sampler is vented from said second sleeve through said passage in said first sleeve to a region above said bath.

* * * * *